US008729287B2

(12) United States Patent
Fridag et al.

(10) Patent No.: US 8,729,287 B2
(45) Date of Patent: May 20, 2014

(54) METHOD FOR PRODUCING 6-CHLORODIBENZO[D,F][1,3,2]-DIOXAPHOSPHEPIN

(75) Inventors: Dirk Fridag, Haltern am See (DE); Robert Franke, Marl (DE); Bernhard Schemmer, Haltern am See (DE); Burkard Kreidler, Recklinghausen (DE); Bjoern Wechsler, Borken (DE)

(73) Assignee: Evonik Oxeno GmbH, Marl (DE)

( * ) Notice: Subject to any disclaimer, the term of this patent is extended or adjusted under 35 U.S.C. 154(b) by 0 days.

(21) Appl. No.: 13/127,184

(22) PCT Filed: Oct. 9, 2009

(86) PCT No.: PCT/EP2009/063150
§ 371 (c)(1),
(2), (4) Date: May 2, 2011

(87) PCT Pub. No.: WO2010/052091
PCT Pub. Date: May 14, 2010

(65) Prior Publication Data
US 2011/0207966 A1  Aug. 25, 2011

(30) Foreign Application Priority Data
Nov. 7, 2008 (DE) .......................... 10 2008 043 584

(51) Int. Cl.
*C07F 9/14* (2006.01)
(52) U.S. Cl.
USPC .................... 558/92; 558/84; 558/95; 568/12
(58) Field of Classification Search
USPC .............................. 568/12, 84; 558/84, 92, 95
See application file for complete search history.

(56) References Cited

U.S. PATENT DOCUMENTS

| 5,391,799 | A | * | 2/1995 | Pastor et al. ..................... 558/96 |
| 7,345,185 | B2 | * | 3/2008 | Ortmann et al. ............... 556/404 |
| 7,767,861 | B2 | | 8/2010 | Ortmann et al. |
| 7,767,867 | B2 | * | 8/2010 | Cortright ....................... 568/861 |
| 8,097,749 | B2 | * | 1/2012 | Miller .............................. 558/96 |
| 2007/0112219 | A1 | * | 5/2007 | Ortmann et al. ................ 568/10 |
| 2007/0117995 | A1 | * | 5/2007 | Ortmann et al. ............... 556/404 |
| 2009/0292146 | A1 | | 11/2009 | Hess et al. |
| 2010/0137623 | A1 | | 6/2010 | Selent et al. |

FOREIGN PATENT DOCUMENTS

| WO | 2005 063776 | 7/2005 |
| WO | 2005 063781 | 7/2005 |
| WO | 2008 012128 | 1/2008 |
| WO | 2008 141853 | 11/2008 |
| WO | 2009 120210 | 10/2009 |
| WO | 2010 052090 | 5/2010 |

OTHER PUBLICATIONS

Korostylev et al; Tetrahedron: Asymmtry 14 (2003) 1905-1909.*
International Search Report issued Jan. 13, 2010 in PCT/EP2009/063150 filed Oct. 9, 2009.
U.S. Appl. No. 13/123,469, filed Apr. 8, 2011, Fridag, et al.
U.S. Appl. No. 13/979,548, filed Aug. 14, 2013, Kreidler, et al.
U.S. Appl. No. 13/979,524, filed Aug. 14, 2013, Kreidler, et al.

* cited by examiner

*Primary Examiner* — Sudhakar Katakam
*Assistant Examiner* — Pancham Bakshi
(74) *Attorney, Agent, or Firm* — Oblon, Spivak, McClelland, Maier & Neustadt, L.L.P.

(57) ABSTRACT

The invention relates to a method for producing 6-chlorodibenzo[d,f][1,3,2]dioxaphosphepin (formula 1), comprising the following steps: a) addition of 2,2'-dihydroxybiphenyl, which is suspended in an inert solvent. into a reactor to an excess of phosphorous trichloride under inert gas and stirring; b) discharge and neutralization of the resulting gases from the reaction mixture; c) separation of the excess phosphorous trichloride and the solvent; d) obtention of 6-chlorodibenzo[d,f][1,3,2]dioxaphosphepin.

19 Claims, No Drawings

METHOD FOR PRODUCING 6-CHLORODIBENZO[D,F][1,3,2]-DIOXAPHOSPHEPIN

The invention relates to a process for preparing 6-chlorodibenzo[d,f][1,3,2]dioxaphosphepin, compound 1.

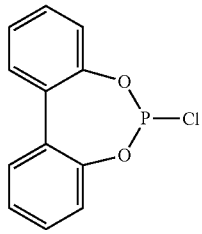

1

Compound 1 is a building block which plays an important role in, inter alia, the synthesis of ligands.

An example of such a ligand is the compound 2, 6,6'-[(3,3'-di-tert-butyl-5,5'-dimethoxy-1,1'-biphenyl-2,2'-diyl)bis(oxy)]bis(dibenzo[d,f][1,3,2]dioxaphosphepin), referred to as biphephos, which has found widespread use in transition metal-catalyzed reactions.

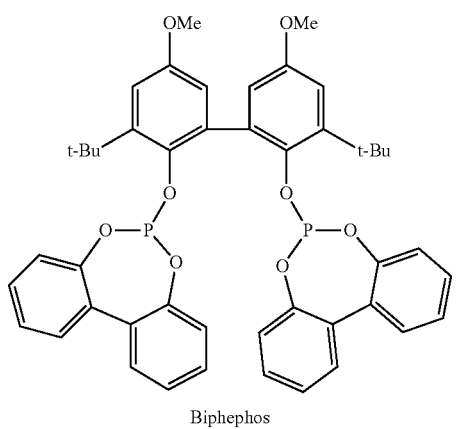

Biphephos

2

The compound 2 is used, for example, in the transition metal-catalyzed hydroaminomethylation (E. Petricci, A. Mann, J. Salvadori, M. Taddei, Tetrahedron Letters 2007, 48, 8501-8504), hydrocyanation (U.S. Pat. No. 5,449,807), hydroformylation (U.S. Pat. No. 4,769,498, CN1986055), isomerization (U.S. Pat. No. 5,440,067) and cyclohydrocarbonylation (U.S. Pat. No. 5,962,744) of olefins.

Compound 2 is usually prepared from commercially available starting materials in three synthesis steps: to produce the backbone, 3-tert-butyl-4-hydroxyanisole is oxidized to the biaryl compound 3,3'-tert-butyl-2,2'-dihydroxy-5,5'-dimethoxybiphenyl. To produce the side wings, phosphorus trichloride is reacted with 2,2'-dihydroxybiphenyl to form compound 1. Finally, the reaction products of the two steps mentioned are condensed with one another in the presence of a base to form biphephos 2.

All processes known hitherto for preparing compound 1 (6-chlorodibenzo[d,f][1,3,2]dioxaphosphepin) lead to formation of undesirable by-products and thus a reduced yield or else require a high outlay in terms of energy or time.

Thus, in U.S. Pat. No. 4,769,498 phosphorus trichloride is added dropwise to 2,2'-dihydroxybiphenyl, forming phosphitic by-products which can be substantially suppressed only by energy-intensive thermal equilibration for a number of hours (cf. L. Anschütz, W. Marquardt, Chem. Ber. 1956, 89, 1119-1123) or/and a complicated vacuum distillation of the product has to be carried out, requiring either very high temperatures (ibid and in L. V. Verizhnikov and P. A. Kirpichnkov, Zh. Obshch. Khim., 1967, 37, 1355) or vacuums of 130 Pa and less which are difficult to realize industrially (EP 0 730 574 and V. N. Tsarev, A. A. Kabro, S. K. Moiseev, V. N. Kalinin, O. G. Bondarev, V. A. Davankov, K. N. Gavrilov, Russ. Chem. Bull., Int. Ed. Vol. 53, 2004, 814-818).

In CN1986055, on the other hand, an excess of phosphorus trichloride is placed in a reaction vessel and 2,2'-dihydroxybiphenyl is added thereto. However, further details regarding the manner of the addition, and also the reaction conditions for a compound which is as highly reactive toward phosphorus trichloride as 2,2'-dihydroxybiphenyl are not provided. Compound 1 is separated from the reaction mixture and purified further by means of vacuum distillation, but once again further details such as pressure and temperature range are absent. The yield of 1 is only 71%. Closer characterization of 1 is not disclosed.

The analogous process disclosed in FR 2873696 requires energy-intensive cooling of the reaction mixture to 0° C. in order to obtain sufficient selectivity and the addition of an amine to scavenge the hydrogen chloride gas formed, with the consequence that an amine hydrochloride which has to be filtered off is formed. However, since the entire reaction mixture is highly corrosive, it requires an expensive filtration apparatus (because it has to be corrosion resistant), for example a filtration apparatus made of DIN 2.4610 alloys. In addition, the amine hydrochloride waste formed has to be disposed of or recycled, which is expensive.

Furthermore, the authors have established that in the process in tetrahydrofuran described by A. van Rooy, P. C. J. Kamer, P. W. N. M. van Leeuwen, K. Goubitz, J. Fraanje, N. Veldman and A. L. Spek in Organometallics 1996, 15, 835-847, the addition of base described there is not permissible since otherwise up to 10%, of by-products formed by acid cleavage of tetrahydrofuran could be formed. However, the necessary addition of an amine once again requires the expensive filtration and/or a vacuum distillation.

Furthermore, apart from the aspects product yield and purity, it is critical that the addition of the 2,2'-dihydroxybiphenyl is carried out in such a way that the removal of heat from this condensation reaction is carried out in a controlled way in order for the process of the invention to be carried out safely, especially with a view to implementation as an industrial process.

In Zh. Obshch. Khim., 1967, 37, 1355, L. V. Verizhnikov and P. A. Kirpichnkov report a process variant in which the starting materials phosphorus trichloride and 2,2'-dihydroxybiphenyl are mixed at room temperature, heated to boiling and the product is subsequently separated off by high-vacuum distillation. Since two highly reactive compounds are mixed directly there, the criterion of controlled heat removal can no longer be guaranteed in the case of large batches. The heat of reaction is −54 kJ/mol and the reaction is therefore strongly exothermic. However, controlled heat removal is absolutely necessary on an industrial scale for safety reasons. Otherwise, the entire quantity of heat could be liberated suddenly on direct mixing of two highly reactive compounds. This quantity of heat can still be removed without danger in the case of small laboratory batches, but in the case of reactions on an industrial scale there is a considerable hazard potential.

It is therefore an object of the invention to develop a process which provides compound 1 from 2,2'-dihydroxybiphenyl and phosphorus trichloride in high yield and purity without making recourse to energy-intensive equilibration or cooling operations and makes do without product distillation, addition of base or use of tetrahydrofuran. In the ideal case, the process can also be managed safely on an industrial scale.

It has been found that this object can be achieved by a process for preparing 6-chlorodibenzo[d,f][1,3,2]dioxaphosphepin, which comprises the following steps:
a) addition of 2,2'-dihydroxybiphenyl suspended in an inert solvent to an excess of phosphorus trichloride under inert gas in a reactor and stirring;
b) discharge and neutralization of the resulting gases from the reaction mixture;
c) removal of the excess phosphorus trichloride and also of the solvent, preferably after the end of the reaction;
d) isolation of 6-chlorodibenzo[d,f][1,3,2]dioxaphosphepin.

The addition of the 2,2'-dihydroxybiphenyl as a suspension in an inert solvent to an excess of phosphorus trichloride is critical to the process of the invention. In particular, a 2- to 25-fold, preferably 10- to 15-fold, excess of phosphorus trichloride, based on molar ratios, is present here. The addition of 2,2'-dihydroxybiphenyl is particularly preferably carried out in a pressure range from 0.07 to 0.12 MPa. For the purposes of the present invention, inert solvents are in principle all solvents which are stable and unreactive under the conditions mentioned. The inert solvent is preferably an aromatic hydrocarbon or hydrocarbon mixture, for example xylenes or toluene, in particular, toluene. In the case of aromatic hydrocarbon mixtures, these preferably contain predominantly toluene, in particular more than 50% by weight of toluene. Additions of suspensions are usually difficult to carry out industrially since settling solid particles quickly lead to blockage of feed lines. This suspension is preferably set to the following value ranges of the following parameters, where:
the solids content of the suspension varies within a range from ≥10 to 60% by mass and
at least 90% of the particles of the suspended 2,2'-dihydroxybiphenyl have a size of ≥1 to ≤1000 microns.

The control and monitoring of these parameters is ensured, for example, by means of commercially available laser light scattering, which is adequately known to those skilled in the art. When the solids content approaches, for example, the lower limit, the suspension can be mixed again by renewed stirring and the solids content can thus be increased again.

After the reaction is complete, excess phosphorus trichloride and the inert solvent or solvents, preferably containing predominantly toluene, are removed. This removal is preferably carried out by means of distillation, preferably under sub-atmospheric pressure which is particularly preferably a fractional distillation. Recovered phosphorus trichloride and the solvent are reused in the synthesis process. Compound 1 remains in approximately quantitative yield and in high purity.

This embodiment of the invention surprisingly shows that only minimal amounts of by-products are formed at ambient temperature and without addition of base and that the sedimentation rate of 2,2'-dihydroxybiphenyl in toluene is so low that no troublesome blockage processes or lump formation processes are observed even in the case of only gentle stirring in the feed reservoir.

Even without further details, it is assumed that a person skilled in the art can utilize the above description in its widest scope. The preferred embodiments and examples are therefore to be interpreted merely as descriptive disclosures which do not limit the invention in any way. The present invention is illustrated below with the aid of examples. Alternative embodiments of the present invention can be obtained in an analogous way.

EXAMPLE 177.65 g (960 mmol) of pulverulent 2,2'-dihydroxybiphenyl in which at least 90% of the crystals have a particle size in the range from 1 to 1000 microns were suspended in 710.61 g of toluene with stirring in a 1000 ml starting material reservoir which had been made inert by means of nitrogen. Adherence to this particle size distribution is advantageous for the stability of the suspension. The solids content of the suspension of up to 60% was monitored by means of laser light scattering. When this value approached the lower limit of 10% by mass, the upper limit was restored by resuming stirring. 1574 g (11.46 mol) of phosphorus trichloride were placed in a 6000 ml reactor which had been made inert by means of nitrogen. To control the evolution of heat, the 6000 ml reactor was thermostated to 20° C. and stirred. The reactor was connected via a waste air scrubber filled with sodium hydroxide solution to a membrane pump. A working pressure of from 0.07 to 0.09 MPa was set to ensure that gases formed were safely discharged via the waste air scrubber. The starting material reservoir was installed above the reactor and at its lowest point was connected via a glass tube to the lid of the reactor. At the outlet of the starting material reservoir, the flow of suspension was regulated by means of a ball cock. The content of the starting material reservoir was introduced into the reactor over a period of 2.5 hours. The cock had to be opened slightly and closed slightly at times. No blockage or lump formation occurred. After the addition was complete, the mixture was stirred at 20° C. for 15 minutes, after which a clear, slightly yellowish solution was present in the reactor. The reactor was subsequently evacuated to 0.02 MPa and heated to 50° C. Excess phosphorus trichloride and toluene-containing solvent were distilled off into receivers made inert by means of nitrogen. The reaction temperature was increased stepwise to 91° C. After 2.25 hours, the distillation was concluded. A virtually colorless, highly viscous liquid remained.

Yield: >99% of theory. Purity: 98%; determined by GC/MS and $^{31}$P-NMR measurement (500 MHz high-field measurement using 85% orthophosphoric acid as external standard, 1 dissolved in d8-toluene) at a shift of δ=185.21 ppm.

The invention claimed is:
1. A process for preparing 6-chlorodibenzo[d,f]-[1,3,2]dioxaphosphepin, which comprises:
a) adding a suspension of 2,2'-dihydroxybiphenyl in an inert solvent to an excess of phosphorus trichloride under inert gas in a reactor and stirring, to obtain a reaction mixture and resulting gas;
b) discharging and neutralizing the at least one resulting gas from the reaction mixture;
c) removing excess phosphorus trichloride and also the solvent; and
d) isolating 6-chlorodibenzo[d,f]-[1,3,2]dioxaphosphepin, wherein base is not added to the reaction mixture.
2. The process of claim 1, wherein the suspension comprising 2,2'-dihydroxybiphenyl has a solids content in a range from 10 to 60% by mass.
3. The process of claim 1, wherein at least 90% of particles of the 2,2'-dihydroxybiphenyl in the suspension have a particle size of from 1 to 1000 microns.

4. The process of claim 1, wherein the inert solvent comprises an aromatic hydrocarbon or hydrocarbon mixture.

5. The process of claim 4, wherein the aromatic hydrocarbon mixture is present and comprises predominantly toluene.

6. The process of claim 1, wherein the removing of excess phosphorous trichloride and the inert solvent, comprising an aromatic hydrocarbon mixture, is carried out by distillation under subatmospheric pressure.

7. The process of claim 1, further comprising:
reusing phosphorus trichloride and aromatic hydrocarbon removed by fractional distillation in the process.

8. The process of claim 2, wherein at least 90% of particles of the 2,2'-dihydroxybiphenyl in the suspension have a particle size of from 1 to 1000 microns.

9. The process of claim 1, wherein the inert solvent comprises an aromatic hydrocarbon.

10. The process of claim 1, wherein the inert solvent comprises a hydrocarbon mixture.

11. The process of claim 1, wherein the inert solvent comprises more than 50% toluene.

12. The process of claim 1, wherein the inert solvent is toluene.

13. The process of claim 1, wherein the inert solvent comprises xylenes.

14. The process of claim 1, wherein the inert solvent is xylenes.

15. The process of claim 1, wherein the phosphorus trichloride is present in a 2- to 25-fold excess in the adding a), based on molar ratios.

16. The process of claim 1, wherein the phosphorus trichloride is present in a 10- to 15-fold excess in the adding a), based on molar ratios.

17. The process of claim 1, wherein the isolating d) does not comprise distilling 6-chlorodibenzo[d,f]-[1,3,2]dioxaphosphepin.

18. The process of claim 1, wherein equilibration or cooling operation are not employed.

19. The process of claim 1, wherein tetrahydrofuran is not employed as solvent.

* * * * *